(12) United States Patent
Linberg

(10) Patent No.: US 6,386,882 B1
(45) Date of Patent: May 14, 2002

(54) REMOTE DELIVERY OF SOFTWARE-BASED TRAINING FOR IMPLANTABLE MEDICAL DEVICE SYSTEMS

(75) Inventor: Kurt R. Linberg, Eden Prairie, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/437,615

(22) Filed: Nov. 10, 1999

(51) Int. Cl.$^7$ ............................................. G09B 23/28
(52) U.S. Cl. ...................... 434/262; 434/267; 434/272; 607/32
(58) Field of Search ............................... 434/262, 267, 434/272; 607/32

(56) References Cited

U.S. PATENT DOCUMENTS

| | | |
|---|---|---|
| 4,494,950 A | 1/1985 | Fishell |
| 4,886,064 A | 12/1989 | Strandberg |
| 4,987,897 A | 1/1991 | Funke |
| 5,321,618 A | 6/1994 | Gessman |
| 5,434,611 A | 7/1995 | Tamura |
| 5,441,047 A | 8/1995 | David et al. |
| 5,590,057 A | 12/1996 | Fletcher et al. |
| 5,701,904 A | 12/1997 | Simmons et al. |
| 5,752,976 A | 5/1998 | Duffin et al. |
| 5,772,586 A | 6/1998 | Heinonen et al. |
| 5,791,907 A | 8/1998 | Ramshaw et al. |
| 5,810,747 A | 9/1998 | Brudny et al. |
| 5,840,020 A | 11/1998 | Heinonen et al. |
| 5,853,292 A * | 12/1998 | Eggert et la. ............ 434/262 X |
| 5,882,206 A * | 3/1999 | Gillio ........................ 434/262 |
| 6,083,248 A * | 4/2000 | Thompson ................ 607/30 X |
| 6,062,865 A * | 5/2000 | Bailey ..................... 434/262 X |
| 6,074,213 A * | 6/2000 | Hon ........................ 434/262 X |
| 6,157,808 A * | 12/2000 | Hollingsworth ......... 434/350 X |
| 6,193,519 B1 * | 2/2001 | Eggert et al. ............ 434/262 X |
| 6,203,495 B1 * | 3/2001 | Bardy ........................ 600/301 |
| 6,263,245 B1 * | 7/2001 | Snell ........................ 607/60 X |

FOREIGN PATENT DOCUMENTS

WO    WO 99/14882    3/1999

OTHER PUBLICATIONS

Downs, Hunter J., III, et al. "IRNS: A System for Telerobotic Surgical Mentoring". 1998. Eleventh IEEE Symposium on Computer–Based Medical Systems, pp. 182–186.*

* cited by examiner

Primary Examiner—Valencia Martin-Wallace
Assistant Examiner—Chanda Harris
(74) Attorney, Agent, or Firm—Girma Wolde-Michael

(57) ABSTRACT

A system and method for remote delivery of software-based simulated training and certification for technicians/operators involved in the management of programmers, programmer-IMD interface and related procedures is disclosed. Preferably a web-based expert data center directs the software-based simulated training and certification which is remotely imported to a programmer. The programmer or equivalent device is coupled to the web-based expert data center via preferably one of many data communication systems. A set of skill-based training activities corresponding to a plurality of software applications on the programmer is accessible from the programmer. The operator issues a training request from the programmer to the expert data center for a specific software application. The expert data center builds a simulated training module based on the operator's request, and returns the training module to the programmer. The training module executes a simulated skill-based training corresponding to the operator's desired software application. Upon completion of the training module, the training results are analyzed. Thereafter, certification may be issued if the operator scores a passing grade on a test at the end of the training. The training results and certification information are archived on the computer, and the certification is electronically transmitted to a certification authority. Upon certification, the operator is granted access to use the specific software application through an authorization key.

70 Claims, 7 Drawing Sheets

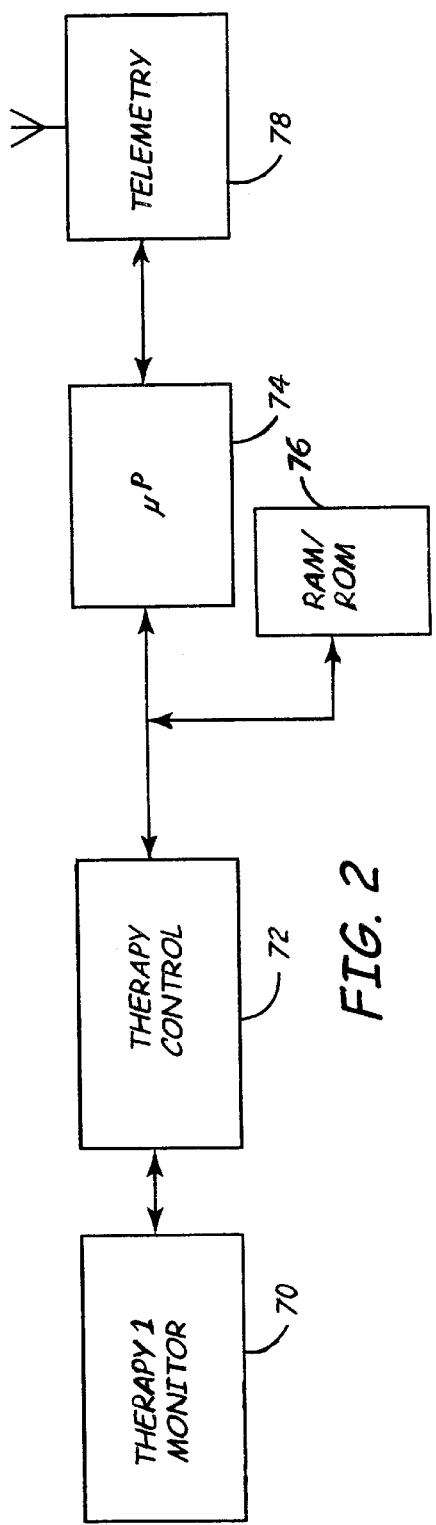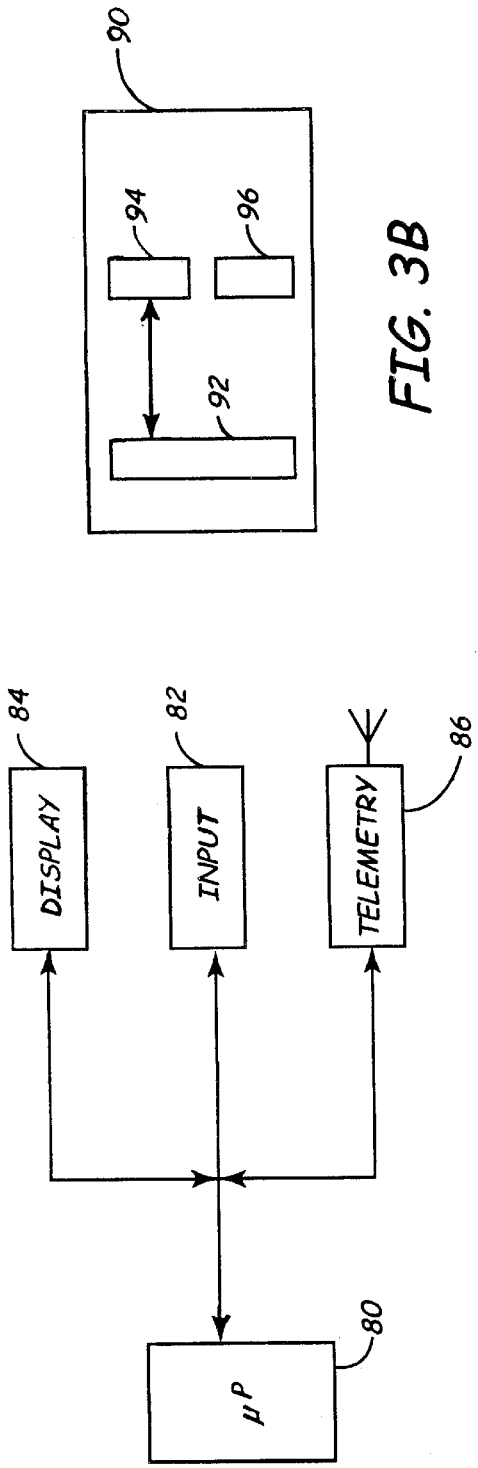

US 6,386,882 B1

REMOTE DELIVERY OF SOFTWARE-BASED TRAINING FOR IMPLANTABLE MEDICAL DEVICE SYSTEMS

THE FIELD OF THE INVENTION

The present invention relates to medical device systems. Specifically, the invention pertains to a remote bi-directional communications with one or more programmable devices, or related controls that are associated with implantable medical devices (IMDs). More specifically, the invention relates to an integrated system and method of bi-directional telecommunications between a web-based expert data center and at least one programmer, utilizing various types of network platforms and architecture to implement, in the programmer, distance-based interrogation, self-identification of specific components, delivery of software-based training applications with automated support for certification generation, certification notification, and related enabling software applications.

BACKGROUND OF THE INVENTION

A technology-based health care system that fully integrates the technical and social aspects of patient care and therapy should be able to flawlessly connect the client with care providers irrespective of separation distance or location of the participants. While clinicians will continue to treat patients in accordance with accepted modern medical practice, developments in communications technology are making it ever more possible to provide medical services in a time and place independent manner.

Prior art methods of clinical services are generally limited to in-hospital operations. For example, if a physician needs to review the performance parameters of an implantable device in a patient, it is likely that the patient has to go to the clinic. Further, if the medical conditions of a patient with an implantable device warrant a continuous monitoring or adjustment of the device, the patient would have to stay in a hospital indefinitely. Such a continued treatment plan poses both economic and social problems. Under the exemplary scenario, as the segment of the population with implanted medical devices increases many more hospitals/clinics including service personnel will be needed to provide in-hospital service for the patients, thus escalating the cost of healthcare. Additionally the patients will be unduly restricted and inconvenienced by the need to either stay in the hospital or make very frequent visits to a clinic.

Yet another condition of the prior art practice requires that a patient visit a clinic center for occasional retrieval of data from the implanted device to assess the operations of the device and gather patient history for both clinical and research purposes. Such data is acquired by having the patient in a hospital/clinic to down load the stored data from the implantable medical device. Depending on the frequency of data collection this procedure may pose serious difficulty and inconvenience for patients who live in rural areas or have limited mobility. Similarly, in the event a need arises to upgrade the software of an implantable medical device, the patient will be required to come into the clinic or hospital to have the upgrade installed. Further, in medical practice it is an industry-wide standard to keep an accurate record of past and temporaneous procedures relating to an IMD uplink with, for example, a programmer. It is required that the report contain the identification of all the medical devices involved in any interactive procedure. Specifically, all peripheral and major devices that are used in down linking to the IMD need to be reported. Currently, such procedures are manually reported and require an operator or a medical person to diligently enter data during each procedure. One of the limitations of the problems with the reporting procedures is the fact that it is error prone and requires rechecking of the data to verify accuracy.

Yet a further condition of the prior art relates to the operator-programmer interface. Generally a medical device manager/technician, should be trained on the clinical and operational aspects of the programmer. Current practice requires that an operator attend a class/session sponsored by a clinic, hospital or the manufacturer to successfully manage a programmer-IMD procedure. Further, the manager should be able to keep abreast of new developments and new procedures in the management, maintenance and upgrade of the IMD. Accordingly it is imperative that operators of programmers, IMDs and related medical devices be trained on a regular basis.

IMDS, programmers and related medical devices are distributed throughout the world. Further, the number of people with implanted medical devices has been increasing over the last few years. Thus, it is impractical to request operators of these globally distributed medical devices to attend training sessions further away from their geographical location. Specifically, at current global distribution levels training centers will need to be located throughout the world. Clearly, such a solution is both expensive and impractical.

A further limitation of the prior art relates to the management of multiple medical devices in a single patient. Advances in modern patient therapy and treatment have made it possible to implant a number of devices in a patient. For example, IMDs such as a defibrillator or a pacer, a neural implant, a drug pump, a separate physiologic monitor and various other IMDs may be implanted in a single patient. To successfully manage the operations and assess the performance of each device in a patient with multi-implants requires a continuous update and monitoring of the devices. Further, it may be preferred to have an operable communication between the various implants to provide a coordinated clinical therapy to the patient. Thus, there is a need to monitor the IMDs including the programmer on a regular, if not a continuous, basis to ensure optimal patient care. In the absence of other alternatives, this imposes a great burden on the patient if a hospital or clinic is the only center where the necessary upgrade, follow up, evaluation and adjustment of the IMDs could be made. Further, even if feasible, the situation would require the establishment of multiple service areas or clinic centers to support the burgeoning number of multi-implant patients world-wide.

Accordingly it is vital to have a programmer unit that would connect to a remote expert data center, a remote web-based data center or a remote data center, all these terms being alternate equivalents as used herein, to provide access to an expert system and import the expertise to a local environment. Further, it is important to have a local program operator/manager or technician who could be trained remotely by exporting a software-based training regimen, from a remote web-based data center, with automated features to provide on site certification generation, certification notification and enabling software. More specifically, it is most desirable to provide globally distributed technicians of programmers, a software-based training which would train, test and certify the technician consistent with the standards set by the manufacturer of the IMD and the programmer and, as well, in compliance with the certification regulation of the country in which the technician is located.

The proliferation of patients with multi-implant medical devices worldwide has made it imperative to provide remote services to the IMDs and timely clinical care to the patient. Frequent use of programmers to communicate with the IMDs and provide various remote services, consistent with co-pending applications titled "Apparatus and Method for Remote Troubleshooting, Maintenance and Upgrade of implantable Device Systems," filed on Oct. 26, 1999, Ser. No. 09/426,741; "Tactile Feedback for Indicating Validity of Communication Link with an Implantable Medical Device," filed Oct. 29, 1999, Ser. No. 09/430,708; "Apparatus and Method for Automated Invoicing of Medical Device Systems," filed Oct. 29, 1999, Ser. No. 09/430,208; "Apparatus and Method for Remote Self-Identification of Components in Medical Device Systems," filed Oct. 29, 1999, Ser. No. 09/429,956; "Apparatus and Method to Automate Remote Software Updates of Medical Device Systems," filed Oct. 29, 1999, Ser. No. 09/429,960; "Method and Apparatus to Secure Data Transfer From Medical Device Systems," filed Nov. 2, 1999, Ser. No. 09/431,881; "Implantable Medical Device Programming Apparatus Having An Auxiliary Component Storage Compartment," filed Nov. 4, 1999, Ser. No. 09/433,477; which are all incorporated by reference herein in their entirety, has become an important aspect of patient care. Thus, in light of the referenced disclosures, remote training of the technicians/operators of the programmers and other peripheral equipment, that are associated with the IMDs, is a vital step in providing efficient therapy and clinical care to the patient.

The prior art provides various types of remote sensing and communications with an implanted medical device. One such system is, for example, disclosed in Funke, U.S. Pat. No. 4,987,897 issued Jan. 29, 1991. This patent discloses a system that is at least partially implanted into a living body with a minimum of two implanted devices interconnected by a communication transmission channel. The invention further discloses wireless communications between an external medical device/programmer and the implanted devices.

One of the limitations of the system disclosed in the Funke patent includes the lack of communication between the implanted devices, including the programmer, with a remote clinical station. If, for example, any assessment, monitoring or maintenance is required to be performed on the IMD the patient will have to go to the remote clinic station or the programmer device needs to be brought to the patient's location. More significantly, the operational worthiness and integrity of the programmer cannot be evaluated remotely thus making it unreliable over time as it interacts with the IMD.

Yet another example of sensing and communications system with a plurality of interactive implantable devices is disclosed by Stranberg in U.S. Pat. No. 4,886,064, issued Dec. 12, 1989. In this disclosure, body activity sensors, such as temperature, motion, respiration and/or blood oxygen sensors, are positioned in a patient's body outside a pacer capsule. The sensors wirelessly transmit body activity signals, which are processed by circuitry in the heart pacer. The heart pacing functions are influenced by the processed signals. The signal transmission is a two-way network and allows the sensors to receive control signals for altering the sensor characteristics.

One of the many limitations of Stranberg is the fact that although there is corporeal two-way communications between the implantable medical devices, and the functional response of the heart pacer is processed in the pacer after collecting input from the other sensors, the processor is not remotely programmable. Specifically, the system does not lend itself to web-based communications to enable remote troubleshooting, maintenance and upgrade from outside the patient's body because the processor/programmer is internally located in the patient forming an integral part of the heart pacer.

Yet another prior art reference provides a multi-module medication delivery system as disclosed by Fischell in U.S. Pat. No. 4,494,950 issued Jan. 22, 1985. The disclosure relates to a system consisting a multiplicity of separate modules that collectively perform a useful biomedical purpose. The modules communicate with each other without the use of interconnecting wires. All the modules may be installed intracorporeal or mounted extracorporeal to the patient. In the alternate, some modules may be intracorporeal with others being extracorporeal. Signals are sent from one module to the other by electromagnetic waves. Physiologic sensor measurements sent from a first module cause a second module to perform some function in a closed loop manner. One extracorporeal module can provide electrical power to an intracorporeal module to operate a data transfer unit for transferring data to the external module.

The Fischell disclosure provides modular communication and cooperation between various medication delivery systems. However, the disclosure does not provide an external programmer with remote sensing, remote data management and maintenance of the modules. Further, the system does neither teach nor disclose an external programmer for telemetrically programming the modules.

Yet another example of remote monitoring of implanted cardioverter defibrillators is disclosed by Gessman in U.S. Pat. No. 5,321,618 issued. In this disclosure a remote apparatus is adapted to receive commands from and transmit data to a central monitoring facility over telephone communication channels. The remote apparatus includes equipment for acquiring a patient's ECG waveform and transmitting that waveform to the central facility over the telephone communications channels. The remote apparatus also includes a segment, responsive to a command received from the central monitoring facility, for enabling the emission of audio tone signals from the cardioverter defibrillator. The audio tones are detected and sent to the central monitoring facility via the telephone communication channel. The remote apparatus also includes patient alert devices, which are activated by commands received from the central monitoring facility over the telephone communication channel.

One of the many limitations of the apparatus and method disclosed in the Gessman patent is the fact that the segment, which may be construed to be equivalent to a programmer, is not remotely adjustable from the central monitoring device. The segment merely acts as a switching station between the remote apparatus and the central monitoring station.

An additional example of prior art practice includes a packet-based telemedicine system for communicating information between central monitoring stations and a remote patient monitoring station disclosed in Peifer, WO 99/14882 published Mar. 25, 1999. The disclosure relates to a packet-based telemedicine system for communicating video, voice and medical data between a central monitoring station and a patient that is remotely located with respect to the central monitoring station. The patient monitoring station obtains digital video, voice and medical measurement data from a patient and encapsulates the data in packets and sends the packets over a network to the central monitoring station. Since the information is encapsulated in packets, the information can be sent over multiple types or combination of network architectures, including a community access television (CATV) network, the public switched telephone network (PSTN), the integrated services digital network (ISDN), the Internet, a local area network (LAN), a wide area network (WAN), over a wireless communications network, or over asynchronous transfer mode (ATM) network. A separate transmission code is not required for each different type of transmission media.

One of the advantages of the Pfeifer invention is that it enables data of various forms to be formatted in a single packet irrespective of the origin or medium of transmission. However, the data transfer system lacks the capability to remotely debug the performance parameters of the medical interface device or the programmer. Further, Pfeifer does not disclose a method or structure by which the devices at the patient monitoring station may be remotely updated, maintained and tuned to enhance performance or correct errors and defects.

Another example of a telemetry system for implantable medical devices is disclosed in Duffin et al, U.S. Pat. No. 5,752,976, issued May 19, 1998, incorporated by reference herein in its entirety. Generally, the Duffin et al disclosure relates to a system and method for communicating with a medical device implanted in an ambulatory patient and for locating the patient in order to selectively monitor device function from a remote medical support network. The communications link between the medical support network and the patient communications control device may comprise a world wide satellite network, a cellular telephone network or other personal communications system.

Although the Duffin et al disclosure provides significant advances over the prior art, it does not teach a communications scheme in which a programmer is remotely debugged, maintained, upgraded or modified to ultimately enhance the support it provides to the implantable device with which it is associated. Specifically, the Duffin et al disclosure is limited to notifying remote medical support personnel or an operator about impending problems with an IMD and also enables constant monitoring of the patient's position worldwide using the GPS system. However, Duffin et al does not teach the remote programming scheme contemplated by the present invention.

In a related art, Thompson discloses a patient tracking system in a co-pending application entitled "World-wide Patient Location and Data Telemetry System For Implantable Medical Devices", Ser. No. 09/045,272, filed on Mar. 20, 1998 which is incorporated by reference herein in its entirety. The disclosure provides additional features for patient tracking in a mobile environment worldwide via the GPS system. However, the remote programming concepts advanced by the present invention are not within the purview of the Thompson disclosure because there is no teaching of a web-based environment in which a programmer is remotely evaluated and monitored to effect functional and parametric tune up, upgrade and maintenance as needed.

Yet in another related art, Ferek-Petric discloses a system for communication with a medical device in a co-pending application, Ser. No. 09/348,506 which is incorporated by reference herein in its entirety. The disclosure relates to a system that enables remote communications with a medical device, such as a programmer. Particularly, the system enables remote communications to inform device experts about programmer status and problems, The experts will then provide guidance and support to the remotely to service personnel or operators located at the programmer. The system may include a medical device adapted to be implanted into a patient; a server PC communicating with the medical device; the server PC having means for receiving data transmitted across a dispersed data communication pathway, such as the Internet; and a client PC having means for receiving data transmitted across a dispersed communications pathway from the SPC. In certain configurations the server PC may have means for transmitting data across a dispersed data communication pathway (Internet) along a first channel and a second channel; and the client PC may have means for receiving data across a dispersed communication pathway from the server PC along a first channel and a second channel.

One of the significant teachings of Ferek Petric's disclosure, in the context of the present invention, includes the implementation of communication systems, associated with IMDs that are compatible with the Internet. Specifically the disclosure advances the art of remote communications between a medical device, such as a programmer, and experts located at a remote location using the Internet. As indicated hereinabove, the communications scheme is structured to primarily alert remote experts to existing or impending problems with the programming device so that prudent action, such as early maintenance or other remedial steps, may be timely exercised. Further, because of the early warning or advance knowledge of the problem, the remote expert would be well informed to provide remote advice or guidance to service personnel or operators at the programmer.

While Ferek's invention advances the art in communications systems relating to interacting with a programmer via a communication medium such as the Internet, the system does neither propose nor suggest remote programming, debugging and maintenance of a programmer without the intervention of a service person.

Another disclosure relating to ambulatory patient health monitoring techniques utilizing interactive visual communications is disclosed by Daniel et al in U.S. Pat. No. 5,441,047, issued Aug. 15, 1995. The invention relates to a system in which the patient is monitored by a health care worker at a certain station, while the patient is at a remote location. The patient's condition is monitored in the home using various monitoring devices. The health care worker is placed into interactive visual communication with the patient.

Yet another prior art provides a monitoring method and a monitoring equipment in U.S. Pat. No. 5,840,020 by Pekka et al issued on Nov. 24, 1998. The patent relates to a monitoring equipment including means for receiving a measurement result indicating the patients blood glucose level, and for storing it in memory. In order to improve and facilitate the treatment of the patient, the monitoring equipment further includes means for receiving data concerning the patient's diet, medication and physical strain and for storing it in the memory. A series of calculations are refined to provide predictive values.

Further, another prior art provides a method for monitoring the health of a patient as disclosed in U.S. Pat. No. 5,772,586 issued to Pekka et al on Jun. 30,1998. The disclosure relates to a method for monitoring the health of a patient by utilizing measurements. In order to improve the contact between the patient and the person treating him, the results of the measurements are supplied via a communications device utilizing a wireless data transmission link to a data processing system available to the person monitoring the patient's health. The patient's health is monitored by means of is the data stored in the data processing system.

Yet a further example of a prior art is provided in U.S. Pat. No. 5,701,904 by Simmons et al issued on Dec. 30, 1997 relating to telemedicine instrumentation pack. The invention includes a portable medical diagnostic apparatus for data gathering. A video camera generates signals based on images taken from the visual instruments. Other electronics circuitry generates signals based on output of the audio instrument and data-gathering instruments. The signals are transmitted to a remote site for analysis by medical personnel.

A related prior art is disclosed in U.S. Pat. No. 5,434,611 issued to Tamura on Jul. 18, 1995. The disclosure relates to a health care system which employs a two-way communications antenna television network to permit communication between a doctor and patients at different locations. The system utilizes a community antenna television (CATV) so that the doctor can directly interrogate patients at home, and the patients can be automatically monitored at home using images and voice by the doctor in the medical office, without hindrance to normal CATV broadcasting.

Yet another related prior art is disclosed in U.S. Pat. No. 5,791,907 by Ramshaw issued on Aug. 11, 1998. The disclosure relates to an interactive medical training device including a computer system with a display. The computer is programmed to provide education and training in medical procedures.

Another related prior art is disclosed in U.S. Pat. No. 5,810,747 by Brudny et al. issued on Sep. 22, 1998. The invention relates to an interactive intervention training system used for monitoring a patient. An expert system and neural network determine a goal to be achieved during training.

One of the limitations of Brudny's teachings is the fact that the interactive training does not provide for a programmer type interface between the expert system (remote station) and a plurality of IMDs. Further, there is no software structure or scheme to provide certification and authorization based on training/test results.

Some of the limitations of Ramshaw's disclosure, in light of the present invention, include the fact that there is no teaching of a programmer that is used for training a technician to manage various clinical data and procedures relating to multiple implantable medical devices distributed throughout, based on a remotely transmitted interactive software from a web-based data center.

Further U.S. Pat. No. 5,590,057 by Ruuska et al., issued on Dec. 31, 1996 provides a training and certification system for a user to perform a task. The invention includes an input device, output device and a controller. The controller receives input data from the input device and controls the output displayed on the output device. The system presents a user with a pretest, a module containing instructions, information about a certain portion of the task to be performed, as well as mini-simulations and a variety of questions. The system present a post-test result and determines if the user is certifiable.

Ruuska et al's disclosure relates to training on a task and provides an advance in computer implemented system for training and certifying a trainee to perform a task. However, in light of the present invention, Ruuska et al. has several limitations. Specifically, Ruuska does not disclose a programmer for managing the operations of IMDs. Further, Ruuska does not relate to a highly globally distributed number of programmers on which technicians need to be trained to operate both the programmers and the IMDs. Furthermore, the present invention pertains to technician certification to operate specified software implemented in the programmer(s). Each programmer may manage a plurality of IMDs via, preferably, a telemetric data transmission system. IMD data download, new software installation, patient history, including significant clinical/therapy information are routinely exchanged between the programmer and the IMDs. The globally distributed programmers that manage the IMDs locally are connected, via a bi-directional communications link, to a remote data center to exchange data, voice and video. The remote data center is a universal command/control point in which expert system's reside. Technicians are trained and certified by training modules at the programmer. The training modules are interactive software which are imported by uplinking the programmer to the expert data center. The present invention also enables a certifying authority to issue certificates by directly interacting with either the programmers or the remote data center.

Accordingly, it would be advantageous to provide a system in which a programmer could uplink to a remote expert data center to import enabling software for self-diagnosis, maintenance and upgrade of the programmer. Yet another desirable advantage would be to provide a system to implement the use of remote expert systems to manage a programmer on a real-time basis. A further desirable advantage would be to provide a communications scheme that is compatible with various communications media, to promote a fast uplink of a programmer to remote expert systems and specialized data resources. Yet another desirable advantage would be to provide a high speed communications scheme to enable the transmission of high fidelity sound, video and data to advance and implement efficient remote data management of a clinical/therapy system via a programmer thereby enhancing patient clinical care. Yet a further desirable advantage would be to remotely import a software-based training system for use by local clinicians/operators/technicians using programmers for IMDs distributed throughout the world. Preferably, a remote web-based expert data center would direct, command and control a software-based simulated training and certification for technicians worldwide. As discussed herein below, the present invention provides these and other desirable advantages.

SUMMARY OF THE INVENTION

The present invention generally relates to a communications scheme in which a remote web-based expert data center interacts with a patient having one or more implantable medical devices (IMDs) via an associated external medical device, preferably a programmer, located in close proximity to the IMDs. Some of the most significant advantages of the invention include the use of various communications media between the remote web-based expert data center and the programmer to remotely exchange clinically significant information and ultimately effect real-time parametric and operational changes as needed.

In the context of the present invention, one of the many aspects of the invention includes a real-time access of a programmer to a remote web-based expert data center, via a communication network, which includes the Internet. The operative structure of the invention includes the remote web-based expert data center, in which an expert system is maintained, having a bi-directional real-time data, sound and video communications with the programmer via a broad range of communication link systems. The programmer is in turn in telemetric communications with the IMDs such that the IMDs may uplink to the programmer or the programmer may down link to lo the IMDs, as needed.

In yet another context of the invention, the critical components and embedded systems of the programmer are remotely maintained, debugged and/or evaluated to ensure proper functionality and performance by down linking expert systems and compatible software from the web-based expert data center.

In a further context of the invention, a programmer is remotely monitored, assessed and upgraded as needed by importing expert systems from a remote expert data center via a wireless or equivalent communications system. The operational and functional software of the embedded systems in the programmer may be remotely adjusted, upgraded or changed as apparent. Some of the software changes may ultimately be implemented in the IMDs as needed by down linking from the programmer to the IMDs.

Yet another context of the invention includes a communications scheme that provides a highly integrated and efficient method and structure of clinical information management in which various networks such as Community access Television, Local area Network (LAN), a wide area network (WAN) Integrated Services Digital Network (ISDN), the Public Switched telephone Network (PSTN), the Internet, a wireless network, an asynchronous transfer mode (ATM) network, a laser wave network, satellite, mobile and other similar networks are implemented to transfer voice, data and video between the remote data center and a programmer. In the preferred embodiment, wireless communications systems, a modem and laser wave systems are illustrated as examples only and should be viewed without limiting the invention to these types of communications alone. Further, in the interest of simplicity, the applicants refer to the various communications system, in relevant parts, as a communications system. However, it should be noted that the communication systems, in the context of this invention, are interchangeable and may relate to various schemes of cable, fiber optics, microwave, radio, laser and similar communications or any practical combinations thereof.

Some of the distinguishing features of the present invention include the use of a robust web-based expert data center to manage and tune the operational and functional parameters of a programmer in real-time. Specifically, the invention enables remote diagnosis, maintenance, upgrade, performance tracking, tuning and adjustment of a programmer from a remote location. Although the present invention focuses on the remote real-time monitoring and management of the programmer, some of the changes and upgrades made to the programmer could advantageously be transferred to the IMDs. This is partly because some of the performance parameters of the programmer are functionally parallel to those in the IMDs. Thus, one additional benefit of the present invention is an enhancement of the programmer may be implemented, on a proactive basis, in the IMDs by down linking from the programmer thereby upgrading the IMDs to promote the patient's well being.

Yet one of the other distinguishing features of the invention includes the use a highly flexible and adaptable communications scheme to promote continuous and real-time communications between a remote expert data center and a programmer associated with a plurality of IMDs. The IMDs are structured to share information intracorporeally and may interact with the programmer, as a unit. Specifically, the IMDs either jointly or severally can be interrogated to implement or extract clinical information as required. In other words, all of the IMDs may be accessed via one IMD or, in the alternate, each one of the IMDs may be accessed individually. The information collected in this manner may be transferred to the programmer by up linking the IMDs as needed.

Further, the present invention provides significant advantages over the prior art by enabling remote troubleshooting, maintenance and software upgrade to the programmer. The communications scheme enables remote debugging and analysis on the programmer. In the event a component or software defect is noted, the system is able to check whether a 'remote-fix' is possible. If not, the system broadcasts an alert to an operator thus attending to the problem on a real-time basis. In the execution of this function the communications scheme of the present invention performs, inter alia, a review of usage logs, error logs, power and battery status, data base integrity and the mean time between failures status of all the significant and relevant components. Further, patient history, performance parameter integrity and software status are mined from the programmer's database and analyzed by an analyzer at the remote expert data center.

The invention provides significant compatibility and scalability to other web-based applications such as telemedicine and emerging web-based technologies such as tele-immersion. For example, the system may be adapted to webtop applications in which a webtop unit may be used to uplink the patient to a remote data center for non-critical information exchange between the IMDs and the remote expert data center. In these and other web-based similar applications the data collected, in the manner and substance of the present invention, may be used as a preliminary screening to identify the need for further intervention using the advanced web technologies.

More significantly, the invention provides a system and method to remotely train technicians in the management and operation of a programmer as it relates to IMDs. The technician is trained via software-based simulated training exercises downloaded to the programmer from a remote expert data center. The training scheme is interactive in that the technician/operator could download to practice and qualify to manage certain functional software which govern the programmer-IMD interface or related procedures. As is discussed hereinbelow, the technician of the programmer is an important link between the expert data center, the programmer and the IMDs in the provision of efficient clinical service to patients worldwide.

BRIEF DESCRIPTION OF THE DRAWINGS

The present invention will be appreciated as the same becomes better understood by reference to the following detailed description of the preferred embodiment of the invention when considered in connection with the accompanying drawings, in which like numbered reference numbers designate like parts throughout the figures thereof, and wherein:

FIG. 2 is a block diagram representing the major components of an IMD;

FIG. 3A is a block diagram presenting the major components of a programmer or webtop unit;

FIG. 3B is a block diagram representing a laser transceiver for high speed transmission of voice, video and other data;

DESCRIPTION OF THE PREFERRED EMBODIMENTS

Figure 1:
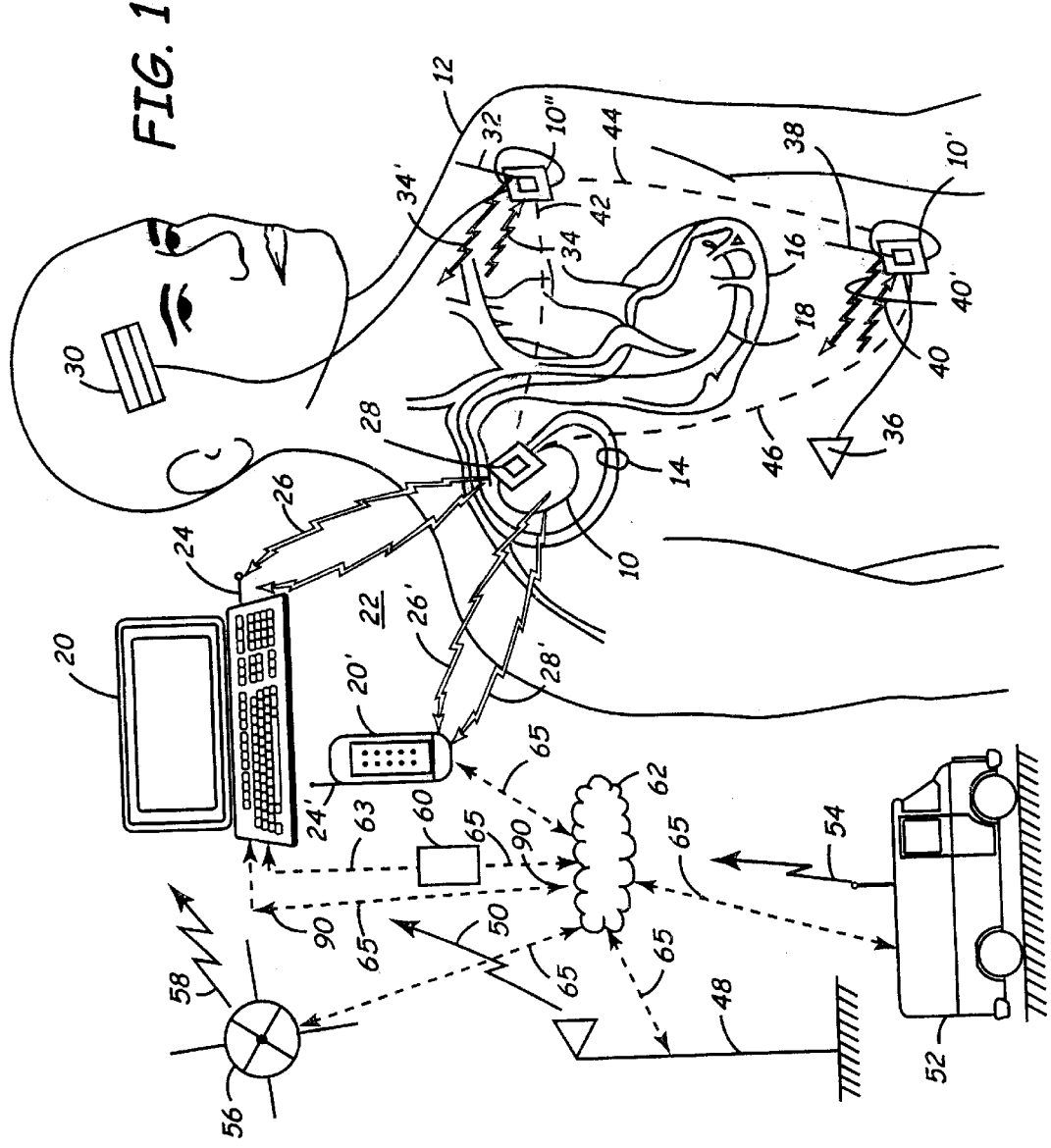
FIG. 1 is a simplified schematic diagram of major uplink and downlink telemetry communications between a remote clinical station, a programmer and a plurality of implantable medical devices (IMDs)

FIG. 1 is a simplified schematic of the major components of the present invention. Specifically, a bi-directional wireless communications system between programmer 20, webtop unit 20' and a number of implantable medical devices (IMDS) represented by IMD 10, IMD 10' and IMD 10" is shown. The IMDs are implanted in patient 12 beneath the skin or muscle. The IMDs are electrically coupled to electrodes 18, 30, and 36 respectively in a manner known in the art. IMD 10 contains a microprocessor for timing, sensing and pacing functions consistent with preset programmed functions. Similarly, IMDs 10' and 10" are microprocessor-based to provide timing and sensing functions to execute the clinical functions for which they are employed. For example, IMD 10' could provide neural stimulation to the brain via electrode 30 and IMD 10" may function as a drug delivery system that is controlled by electrode 36. The various functions of the IMDs are coordinated using wireless telemetry. Wireless links 42, 44 and 46 jointly and severally couple IMDs 10, 10' and 10" such that programmer 20 may transmit commands or data to any or all the of IMDs via one of telemetry antennas 28, 32 and 38. This structure provides a highly flexible and economical wireless communications system between the IMDS. Further, the structure provides a redundant communications system, which enables access to any one of a multiplicity of IMDs in the event of a malfunction of one or two of antennas 28, 32 and 38.

Programming commands or data are transmitted from programmer 20 to IMDs 10, 10' and 10" via external RF telemetry antenna 24. Telemetry antenna 24 may be an RF head or equivalent. Antenna 24 may be located on programmer 20 externally on the case or housing. Telemetry antenna 24 is generally telescoping and may be adjustable on the case of programmer 20. Both programmer 20 and webtop unit 20' may be placed a few feet away from patient 12 and would still be within range to wirelessly communicate with telemetry antennas 28, 32 and 38.

The uplink to remote web-based expert data center 62, hereinafter referred to as, interchangeably, "data center 62", "expert data center 62" or "web-based data center 62" without limitations, is accomplished through programmer 20 or webtop unit 20'. Accordingly programmer 20 and webtop unit 20' function as an interface between IMDs 10, 10' and 10" and data center 62. One of the many distinguishing elements of the present invention includes the use of various scalable, reliable and high-speed wireless communication systems to bi-directionally transmit high fidelity digital/analog data between programmer 20 and data center 62.

There are a variety of wireless mediums through which data communications could be established between programmer 20 or webtop unit 20' and data center 62. The communications link between Programmer 20 or webtop unit 20' and data center 62 could be modem 60, which is connected to programmer 20 on one side at line 63 and data center 62 at line 64 on the other side. In this case, data is transferred from data center 62 to programmer 20 via modem 60. Alternate data transmission systems include, without limitations, stationary microwave and/or RF antennas 48 being wirelessly connected to programmer 20 via tunable frequency wave delineated by line 50. Antenna 48 is in communications with data center 62 via wireless link 65. Similarly, webtop unit 20', mobile vehicle 52 and satellite 56 are in communications with data center 62 via wireless link 65. Further, mobile system 52 and satellite 56 are in wireless communications with programmer 20 or webtop unit 20' via tunable frequency waves 54 and 58, respectively.

In the preferred embodiment a Telnet system is used to wirelessly access data center 62. Telnet emulates a client/server model and requires that the client run a dedicated software to access data center 62. The Telnet scheme envisioned for use with the present invention includes various operating systems including UNIX, Macintosh, and all versions of Windows.

Functionally, an operator at programmer 20 or an operator at data center 62 would initiate remote contact. Programmer 20 is down linkable to IMDs via link antennas 28, 32 and 38 to enable data reception and transmission. For example, an operator or a clinician at data center 62 may downlink to programmer 20 to perform a routine or a scheduled evaluation of programmer 20. In this case the wireless communication is made via wireless link 65. If a downlink is required from programmer 20 to IMD 10 for example, the downlink is effected using telemetry antenna 22. In the alternate, if an uplink is initiated from patient 12 to programmer 20 the uplink is executed via wireless link 26. As discussed herein below, each antenna from the IMDs can be used to uplink all or one of the IMDs to programmer 20. For example, IMD 10" which relates to neural implant 30 can be implemented to up-link, via wireless antenna 34 or wireless antenna 34', any one, two or more IMDs to programmer 20. Preferably bluetooth chips, adopted to function within the body to outside the body and also adopted to provide low current drain, are embedded in order to provide wireless and seamless connections 42, 44 and 46 between IMDs 10,10' and 10". The communication scheme is designed to be broadband compatible and capable of simultaneously supporting multiple information sets and architecture, transmitting at relatively high speed, to provide data, sound and video services on demand.

FIG. 2 illustrates typical components of an IMD, such as those contemplated by the present invention. Specifically, major operative structures common to all IMDs 10, 10' and 10" are represented in a generic format. In the interest of brevity, IMD 10 relative to FIG. 2 refers to all the other IMDs. Accordingly, IMD 10 is implanted in patient 12 beneath the patient's skin or muscle and is electrically coupled to heart 16 of patient 12 through pace/sense electrodes and lead conductor(s) of at least one cardiac pacing lead 18 in a manner known in the art. IMD 10 contains timing control 72 including operating system that may employ microprocessor 74 or a digital state machine for timing, sensing and pacing functions in accordance with a programmed operating mode. IMD 10 also contains sense amplifiers for detecting cardiac signals, patient activity sensors or other physiologic sensors for sensing the need for cardiac output, and pulse generating output circuits for delivering pacing pulses to at least one heart chamber of heart 16 under control of the operating system in a manner well known in the prior art. The operating system includes memory registers or RAM/ROM 76 for storing a variety of programmed-in operating mode and parameter values that are used by the operating system. The memory registers or RAM/ROM 76 may also be used for storing data compiled from sensed cardiac activity and/or relating to device operating history or sensed physiologic parameters for telemetry out on receipt of a retrieval or interrogation instruction. All of these functions and operations are well known in the art, and many are generally employed to store operating commands and data for controlling device operation and for later retrieval to diagnose device function or patient condition.

Programming commands or data are transmitted between IMD 10 RF telemetry antenna 28, for example, and an external RF telemetry antenna 24 associated with programmer 20. In this case, it is not necessary that the external RF telemetry antenna 24 be contained in a programmer RF head so that it can be located close to the patient's skin overlying IMD 10. Instead, the external RF telemetry antenna 24 can be located on the case of programmer 20. It should be noted that programmer 20 can be located some distance away from patient 12 and is locally placed proximate to the IMDs such that the communication between IMDs 10, 10' and 10" and programmer 20 is telemetric. For example, programmer 20 and external RF telemetry antenna 24 may be on a stand a few meters or so away from patient 12. Moreover, patient 12 may be active and could be exercising on a treadmill or the like during an uplink telemetry interrogation of real-time ECG or other physiologic parameters. Programmer 20 may also be designed to universally program existing IMDs that employ RF telemetry antennas of the prior art and therefore also have a conventional programmer RF head and associated software for selective use therewith.

In an uplink communication between IMD 10 and programmer 20, for example, telemetry transmission 22 is activated to operate as a transmitter and external RF telemetry antenna 24 operates as a telemetry receiver. In this manner data and information may be transmitted from IMD 10 to programmer 20. In the alternate, IMD 10 RF telemetry antenna 26 operates as a telemetry receiver antenna to downlink data and information from programmer 20. Both RF telemetry antennas 22 and 26 are coupled to a transceiver comprising a transmitter and a receiver.

FIG. 3A is a simplified circuit block diagram of major functional components of programmer 20. The external RF telemetry antenna 24 on programmer 20 is coupled to a telemetry transceiver 86 and antenna driver circuit board including a telemetry transmitter and telemetry receiver 34. The telemetry transmitter and telemetry receiver are coupled to control circuitry and registers operated under the control of microcomputer 80. Similarly, within IMD 10, for example, the RF telemetry antenna 26 is coupled to a telemetry transceiver comprising a telemetry transmitter and telemetry receiver. The telemetry transmitter and telemetry receiver in IMD 10 are coupled to control circuitry and registers operated under the control of microcomputer 74.

Further referring to FIG. 3A, programmer 20 is a personal computer type, microprocessor-based device incorporating a central processing unit, which may be, for example, an Intel Pentium microprocessor or the like. A system bus interconnects CPU 80 with a hard disk drive, storing operational programs and data, and with a graphics circuit and an interface controller module. A floppy disk drive or a CD ROM drive is also coupled to the bus and is accessible via a disk insertion slot within the housing of programmer 20. Programmer 20 further comprises an interface module, which includes a digital circuit, a non-isolated analog circuit, and an isolated analog circuit. The digital circuit enables the interface module to communicate with interface controller module. Operation of the programmer in accordance with the present invention is controlled by microprocessor 80.

In order for the physician or other caregiver or operator to communicate with the programmer 20, a keyboard or input 82 coupled to CPU 80 is optionally provided. However the primary communications mode may be through graphics display screen of the well-known "touch sensitive" type controlled by a graphics circuit. A user of programmer 20 may interact therewith through the use of a stylus, also coupled to a graphics circuit, which is used to point to various locations on screen or display 84 which display menu choices for selection by the user or an alphanumeric keyboard for entering text or numbers and other symbols. Various touch-screen assemblies are known and commercially available. Display 84 and or the keyboard comprise means for entering command signals from the operator to initiate transmissions of downlink or uplink telemetry and to initiate and control telemetry sessions once a telemetry link with data center 62 or an implanted device has been established. Display screen 84 is also used to display patient related data and menu choices and data entry fields used in entering the data in accordance with the present invention as described below. Display screen 84 also displays a variety of screens of telemetered out data or real-time data. Display screen 84 may also display plinked event signals as they are received and thereby serve as a means for enabling the operator to timely review link-history and status.

Programmer 20 further comprises an interface module, which includes digital circuit, non-isolated analog circuit, and isolated analog circuit. The digital circuit enables the interface module to communicate with the interface controller module. As indicated hereinabove, the operation of programmer 20, in accordance with the present invention, is controlled by microprocessor 80. Programmer 20 is preferably of the type that is disclosed in U.S. Pat. No. 5,345,362 to Winkler, which is incorporated by reference herein in its entirety.

Screen 84 may also display up-linked event signals when received and thereby serve as a means for enabling the operator of programmer 20 to correlate the receipt of uplink telemetry from an implanted device with the application of a response-provoking action to the patient's body as needed. Programmer 20 is also provided with a strip chart printer or the like coupled to interface controller module so that a hard copy of a patient's ECG, EGM, marker channel of graphics displayed on the display screen can be generated.

As will be appreciated by those of ordinary skill in the art, it is often desirable to provide a means for programmer 20 to adapt its mode of operation depending upon the type or generation of implanted medical device to be programmed and to be compliant with the wireless communications system through which data and information is transmitted between programmer 20 and data center 62.

FIG. 3B is an illustration of the major components of Wave unit 90 utilizing laser technologies such as for example the WaveStar Optic Air Unit, manufactured by Lucent Technologies or equivalent. This embodiment may be implemented for large data transfer at high speed in applications involving several programmers. The unit includes laser 92, transceiver 94 and amplifier 96. A first wave unit 90 is installed at data center 62 and a second unit 90' is located proximate to programmer 20 or webtop unit 20'. Data transmission between remote data center 62 and programmer unit 20 is executed via wave units 90. Typically, the first wave unit 90 accepts data and splits it into unique wavelength for transmission. The second wave unit 90' recomposes the data back to its original form.

Figure 4:
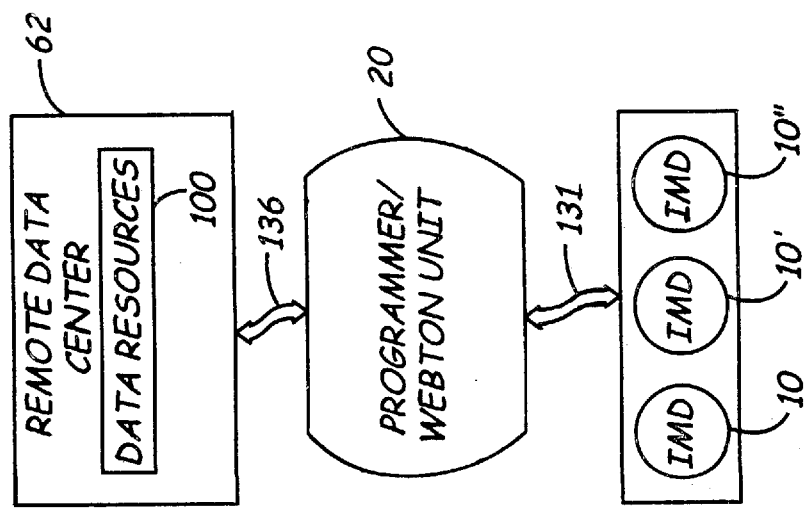
FIG. 4 is a block diagram illustrating the organizational structure of the wireless communication system in accordance with the present invention.

FIG. 4 is a simplified block diagram illustrating the principal systems of the invention. The Remote expert system or data center 62 includes data resource 100. As discussed hereinabove, data center 62 is preferably in wireless communications with programmer 20. The medium of communications between programmer 20 and data center 62 may be selected from one or a combination of several cable and wireless systems discussed hereinabove. Further, programmer 20 is in wireless communications with a number of IMDs, such as shown in FIG. 1. Although three IMDs are shown for illustrative purposes, it should be noted that several IMDs may be implemented and the practice of the present invention does not limit the number of implants per se.

Figure 5:
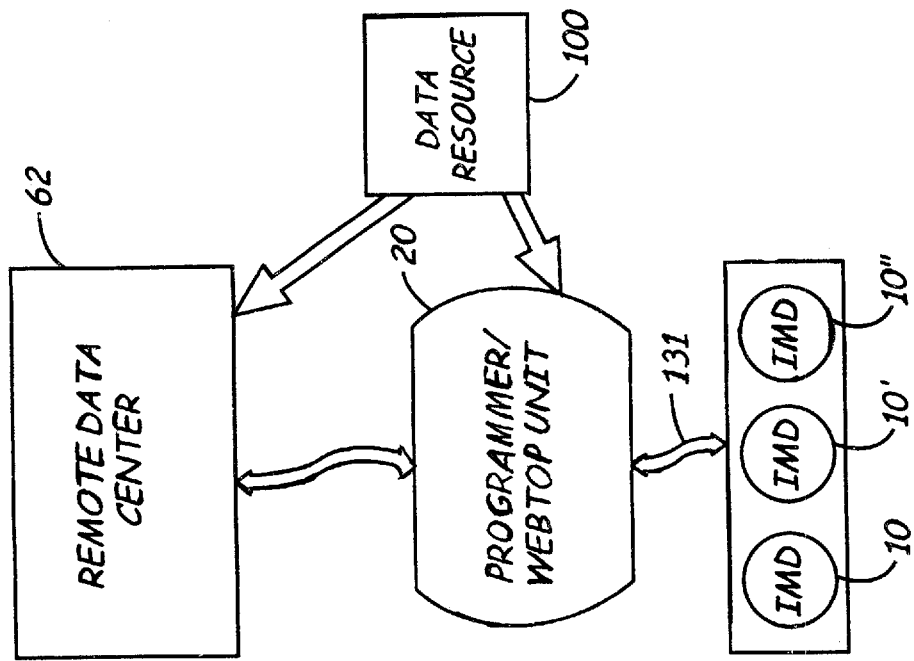
FIG. 5 is a block diagram illustrating an alternate arrangement of the structure depicted in FIG. 4.

FIG. 5 is a representation of the major functional components of Programmer 20, data resources 100 and the wireless data communications 131 and 136. Specifically, as discussed hereinabove, programmer 20 includes power supply 110, disc drive 112, display screen 114, CD ROM 116, printer 118, RAM/ROM 120 and stylus 122. Analyzer 126 is in bi-directional data communications with the other components of programmer 20 and includes disc drive 128, display 130, battery 132 and RAM/ROM 134.

Programmer 20 is connected to remote data center 62 via bi-directional data communication link 136. In FIG. 4 data resource center 100 forms the web-based data resources/expert system 100. Accordingly, data resources system 100 is a sub-component of remote data center 62, which includes information identification module 138, analyzation module 140, data storage module 142 and software update module 146. Notably, in FIG. 5, data resources 100 is located outside remote data center 20 and is in operable data communication with both remote data center 62 and programmer 20.

Referring to programmer 20 in more detail, when a physician or an operator needs to interact with programmer 20, a keyboard coupled to Processor 80 is optionally employed. However the primary communication mode may be through graphics display screen of the well-known "touch sensitive" type controlled by graphics circuit. A user of programmer 20 may interact therewith through the use of a stylus 122, also coupled to a graphics circuit, which is used to point to various locations on screen/display 114 to display menu choices for selection by the user or an alphanumeric keyboard for entering text or numbers and other symbols as shown in the above-incorporated '362 patent. Various touch-screen assemblies are known and commercially available. The display and or the keyboard of programmer 20, preferably include means for entering command signals from the operator to initiate transmissions of downlink telemetry from IMDs and to initiate and control telemetry sessions once a telemetry link with one or more IMDs has been established. The graphics display/screen 114 is also used to display patient related data and menu choices and data entry fields used in entering the data in accordance with the present invention as described below. Graphics display/screen 114 also displays a variety of screens of telemetered out data or real-time data. Programmer 20 is also provided with a strip chart printer 118 or the like coupled to interface controller module so that a hard copy of a patient's ECG, EGM, marker channel or similar graphics display can be generated. Further, Programmer 20's history relating to instrumentation and software status may be printed from printer 118. Similarly, once an uplink is established between programmer 20 and any one of IMDs 10, 10' and 10", various patient history data and IMD performance data may be printed out. The IMDs contemplated by the present invention include a cardiac pacemaker, a defibrillator, a pacer-defibrillator, implantable monitor (Reveal), cardiac assist device, and similar implantable devices for cardiac rhythm and therapy. Further the IMD units contemplated by the present invention include electrical stimulators such as, but not limited to, a drug delivery system, a neural stimulator, a neural implant, a nerve or muscle stimulator or any other implant designed to provide physiologic assistance or clinical therapy.

Data resources 100 represents a high speed computer network system which is located in remote expert data center 62 having wireless bi-directional data, voice and video communications with programmer 20 via wireless communications link 136. Generally data resources 100 are preferably located in a central location and are equipped with high-speed web-based computer networks. Preferably, the data resource center is manned 24-hours by operators and clinical personnel who are trained to provide a web-based remote service to programmer 20. Additionally, as discussed hereinabove, data resources 100 provide remote monitoring, maintenance and upgrade of programmer 20. The location of remote data center 62 and, consequently, the location of data resources 100 are dependent upon the sphere of service. In accordance with the present invention, data resource 100 may be located in a corporate headquarters or manufacturing plant of the company that manufactures programmer 20. Wireless data communications link/connection 136 can be one of a variety of links or interfaces, such as a local area network (LAN), an internet connection, a telephone line connection, a satellite connection, a global positioning system (GPS) connection, a cellular connection, a laser wave generator system, any combination thereof, or equivalent data communications links.

As stated hereinabove, bi-directional wireless communications 136 acts as a direct conduit for information exchange between remote data center 62 and programmer 20. Further, bi-directional wireless communications 136 provides an indirect link between remote data center and IMDs 10, 10' and 10" via programmer 20. In the context of this disclosure the word "data" when used in conjunction with bi-directional wireless communications also refers to sound, video and information transfer between the various centers.

Figure 6:
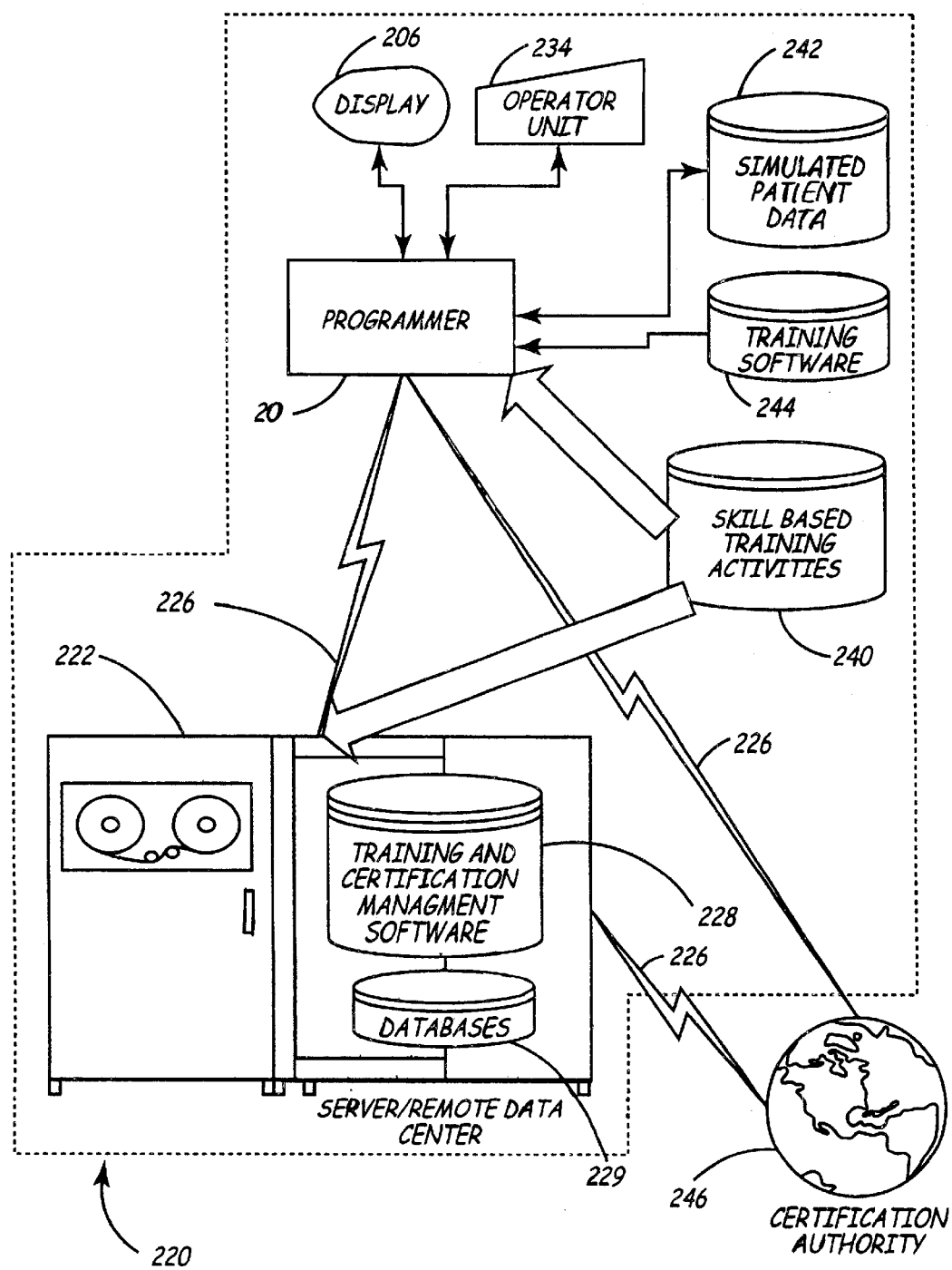
FIG. 6 represents a high level structural organization of the programmer, the remote data center, the certification authority and training software and the communications therein.

FIG. 6 is a detailed block diagram of one embodiment of a system for remote delivery of software-based training for a medical device in accordance with the invention, as shown generally at 220. Server/remote data center 220 includes computer 222 coupled to a remote medical device (i.e., a programmer 20) via information network link 226. An operator may obtain structured, skill-based training and certification on specific software applications for programmer 20 via server/remote data center 220.

Computer 222 is generally a conventional computing system capable of servicing training requests issued by programmer 20. Examples of computer 222 include, but are not limited to: enterprise servers, midrange servers, workstations, or personal computer (PC) servers. Computer 222 has the ability to access training and certification management software 228 and databases 229 for remotely administering skill-based training of software applications on programmer 20. Functions performed by training and certification management software 228 include, but are not limited to: authenticating a training request from the operator of programmer 20, building a training module corresponding to the operator's training request, returning the training module to the programmer, receiving and archiving operator training results and certification information, and notifying a certification authority when an operator achieves certification on a software application. In one embodiment of the invention, training and certification management software 228 is structured to provide a real-time notification to the certification authority, as to the certification status and skill-level of an operator of programmer 20. Training and certification management software 228 is discussed in greater detail with respect to FIG. 7.

Databases 229 include archived operator training results and operator certification data. Databases 229 enable the manufacturer of programmer 20 to maintain up-to-date lists of certified operators of various software applications on programmer 20 distributed throughout the world. Thus, if features are added or changed regarding the software applications on programmer 20, the entire global community of certified operators can be automatically notified of the changes by the manufacturer by broadcasting/notifying the change via information network link 226. Additionally, server databases 229 enable the manufacturer of programmer 20 to accurately track which of the various software applications are most popular with and useful to the operators worldwide.

In one embodiment of the invention, remote delivery system 220 also includes skill-based training activities 240 corresponding to software applications resident on programmer 20. Skill-based training activities 240 enable an operator to undergo a simulated self-paced training on software applications for monitoring patient data. In this embodiment, the operator accesses skill-based training activities 240 from programmer 20 via information network 226.

As discussed above, programmer 20 is a medical device which is coupled to IMD 10 via lead 18. IMDs 10, 10' 10" represent various implantable medical devices, such as cardiac pacemakers, defibrillators, pacemaker/defibrillators, and combinations thereof. Further, IMDs 10, 10' and 10" may represent drug delivery systems, electrical stimulators including nerve and muscle stimulators, deep brain stimulators, or heart assist devices or pumps.

Programmer 20 enables the operator to assess the performance of IMD 10 and its associated circuitry via information link 232. Specifically, procedures involving implantation of IMD 10, programming of IMD 10, and transmission of operational information feedback from IMD 10 are controlled and by monitored by programmer 20. These procedural functions are checked by an operator who manages the various functions of programmer. Generally, the operator utilizes input 234 to initiate the procedure and manages specific procedure(s) via interactive display 206. Programmer 20 includes software applications for monitoring simulated patient data 242. In one embodiment of the present invention, programmer 20 also includes a set of skill-based training activities 240 corresponding to software applications for monitoring patient data 242. Skill-based training activities 240 enable an operator to undergo self-paced training on the software applications for monitoring patient data 242 residing on programmer 20. Finally, programmer 20 includes training software 244 for training the operator in software applications for monitoring patient data 242. Information network link 226 is generally a communications medium capable of enabling the exchange of information between programmer 20 and computer 222. For example, information network link 226 can be a data communication media, such as local area network (LAN) connection, a telephone line connection, an internet connection, a satellite connection, a constellation of satellite connections, a global positioning system (GPS) connection, a laser waveform, or any combination thereof.

After the operator has been certified on one of the software applications for monitoring patient data 242, system 220 electronically notifies an external certification authority 246 identifying the global location of the operator and the level of certification including the type of software. As an example, a regulating authority of a country may require notification that a programmer operator working within that country has achieved certification in the operation of a specific software application for monitoring patient data 242 before the operator is authorized to manage the programmer implementing the specific software application. In one embodiment on the present invention, operator certification notification is delivered, in real-time, to certification authority 246 via electronic mail. In the embodiment shown in FIG. 6, the electronic notification is issued from computer 222 to certification authority 246 via information network link 226 which as previously discussed is a data communication media.

In another embodiment of the invention, the electronic notification is issued directly from programmer 20 to certification authority 246 via information network link 226. The address of certification authority 246 may be stored within computer 222 or programmer 20, or alternatively, the operator may manually provide the electronic address of certification authority 246 by entering the address directly at programmer 20 via operator input 234.

Figure 7:
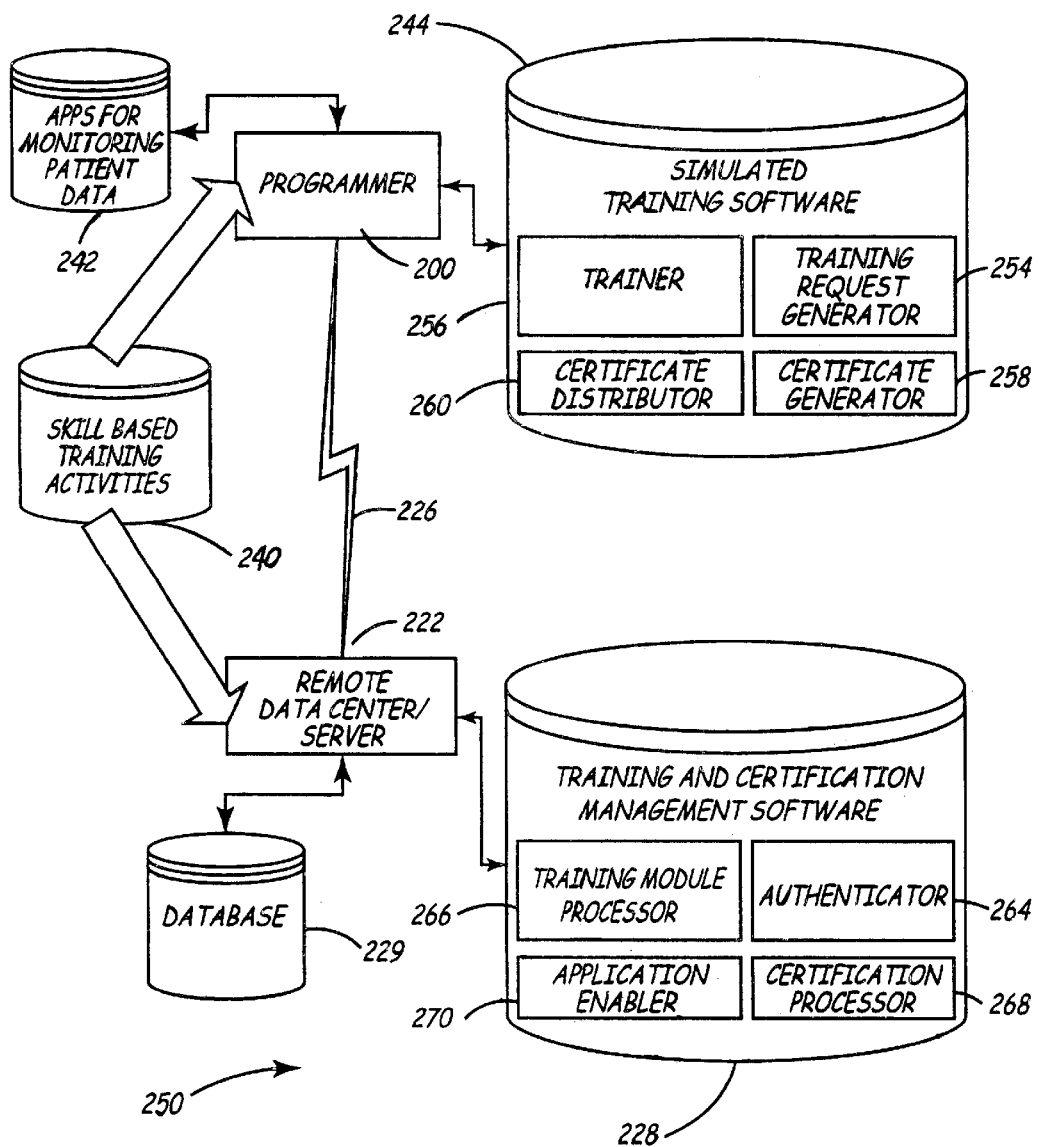
FIG. 7 represents detailed software package schemes and elements thereof implemented in accordance with the invention.

FIG. 7 is a detailed block diagram of one embodiment of a system for remote delivery of software-based training for a medical device in accordance with the invention, shown generally at 250. As previously illustrated in FIG. 7, skill-based training activities 240 can reside on computer 222 and/or programmer 20.

Examples of software applications for monitoring patient data 242 include, but are not limited to: identification of trends of key diagnostic parameters and identification of implantable device parameters that need to be adjusted. Training software 244 includes training request generator 254 which receives an operator training request, processes the request, and transmits the request to computer 222 via information network link 226. Trainer 256, also residing within training software 244, enables the operator to execute a training module corresponding to the operator's training request. Further, training software 244 includes certificate generator 258 which evaluates the operator's performance on the training modules and generating user certification data if the user's performance on the training modules meets or exceeds a pre-defined performance criteria. Furthermore, training software 244 includes certificate distributor 260 which distributes a certificate to certification authority 246 or to computer 222 via information network link 226.

As an illustrative example, the operator is required to complete a fifty question test upon completion of a simulated training module corresponding to the material presented in the training module. If the operator answers at least eighty percent of the questions correctly, certificate generator 258 generates certification data for the operator. Certificate distributor 260 distributes the operator certification data to certification authority 246. As another illustrative example, if the operator achieves certification on a software application for monitoring patient data 242, certificate distributor 260 will distribute the certification information to certification authority 246, or alternatively, to computer 222.

Database 229, residing on computer 222, is used by the manufacturer to track operator training and certification activities for all programmers 20 worldwide. For example, every time computer 222 receives and processes a training request from an operator at a remote programmer 20, an entry is logged in database 229. Additionally, every time an operator achieves certification on a specific application for monitoring software application 242, the certification is recorded in database 229.

Training and certification management software 228 includes authenticator 264 for authenticating operator training requests generated on programmer 20. As an example, authenticator 264 can verify that the operator is qualified to receive the training, and that the requested training in the advanced software application is authorized by a governmental regulatory authority in the country where programmer 20 resides.

Training and certification management software 228 further includes training module processor 266 for processing authenticated operator training requests. In one embodiment of the invention, skill-based training activities 240 reside on programmer 20. Training module processor 266 builds an ordered list of skill-based training activities 240 corresponding to the operator training request, which is transmitted to programmer 20. This list of skill-based training activities 240 is used as input to trainer 256 of training software 244. In another embodiment of the invention, skill-based training activities 240 reside on computer 222. Training module processor 266 transmits a selected set of skill-based training executable programs to programmer 20. In yet another embodiment of the invention, skill-based training activities 240 reside on computer 222. Training module processor 266 transmits an ordered list of paths to the skill-based training executables residing on computer 222.

Training and certification management software 228 also includes certification processor 268 for processing, distributing, and archiving operator certification information generated by programmer 20. In some instances, it may be desirable to distribute certification information to certification authority 246 (FIG. 7) via information network link 226 from computer 222 rather than from certificate distributor 260 of programmer 20. As an example, the address of certification authority 246 may be unknown to the operator, or not stored on programmer 20. Certification authority 246 may also prefer to receive the certification information from computer 222 of the manufacturer for efficiency and/or security reasons.

Finally, training and certification management software 228 includes application enabler 270 for enabling operator access to applications for monitoring patient data 242 residing on programmer 20 for which the operator has achieved certification. In one embodiment of the invention, application enabler 270 transmits an authorization key from computer 222 to the operator of programmer 20 upon operator certification. The operator then uses the authorization key to "unlock" a software application for monitoring patient data 242 on programmer 20. One example of an authorization key is an alphanumeric password.

Figure 8A:
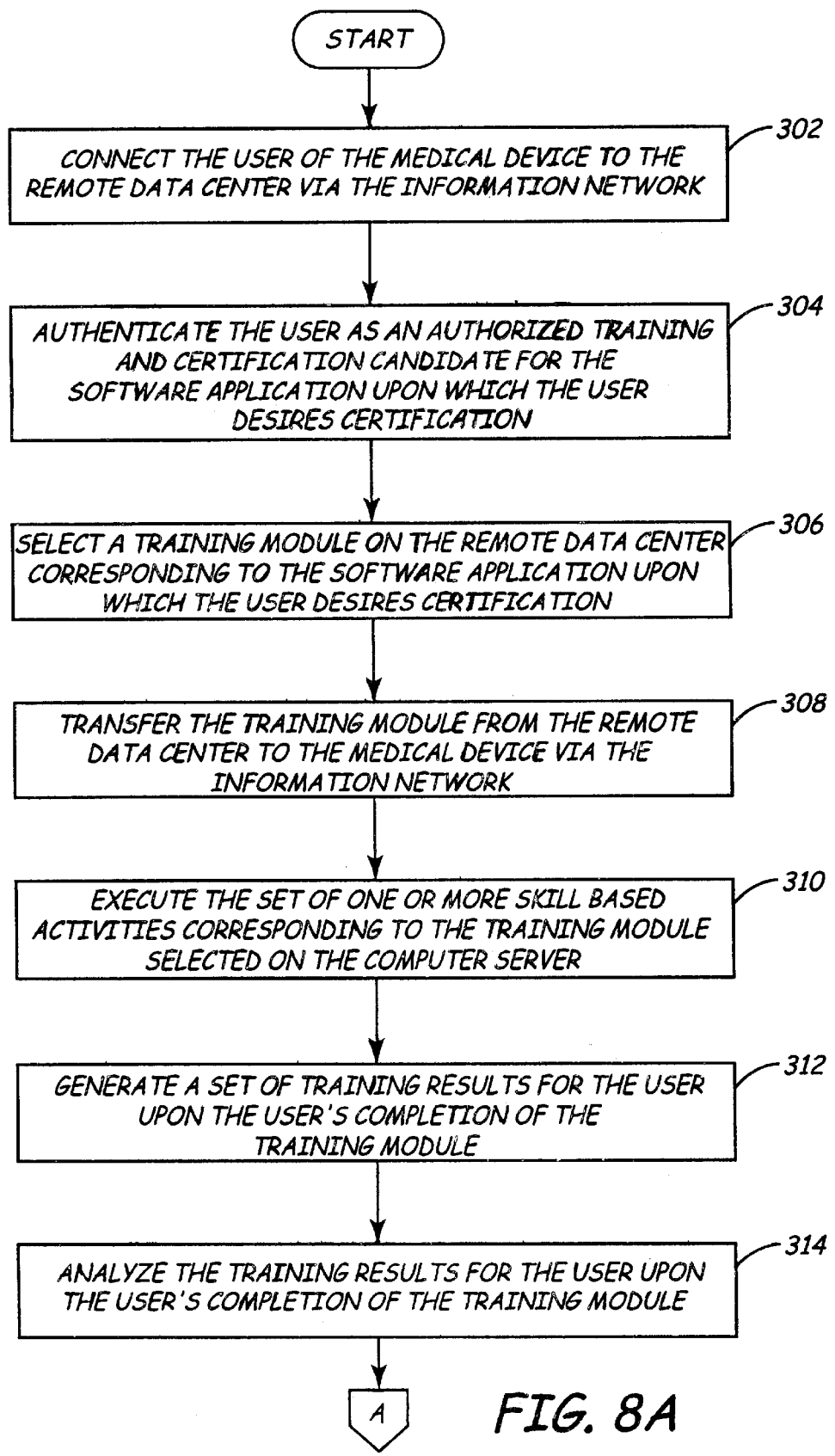
FIGS. 8A and 8B are flow charts representing a method for remote delivery of software-based training for a programmer in accordance with the invention.
Figure 8B:
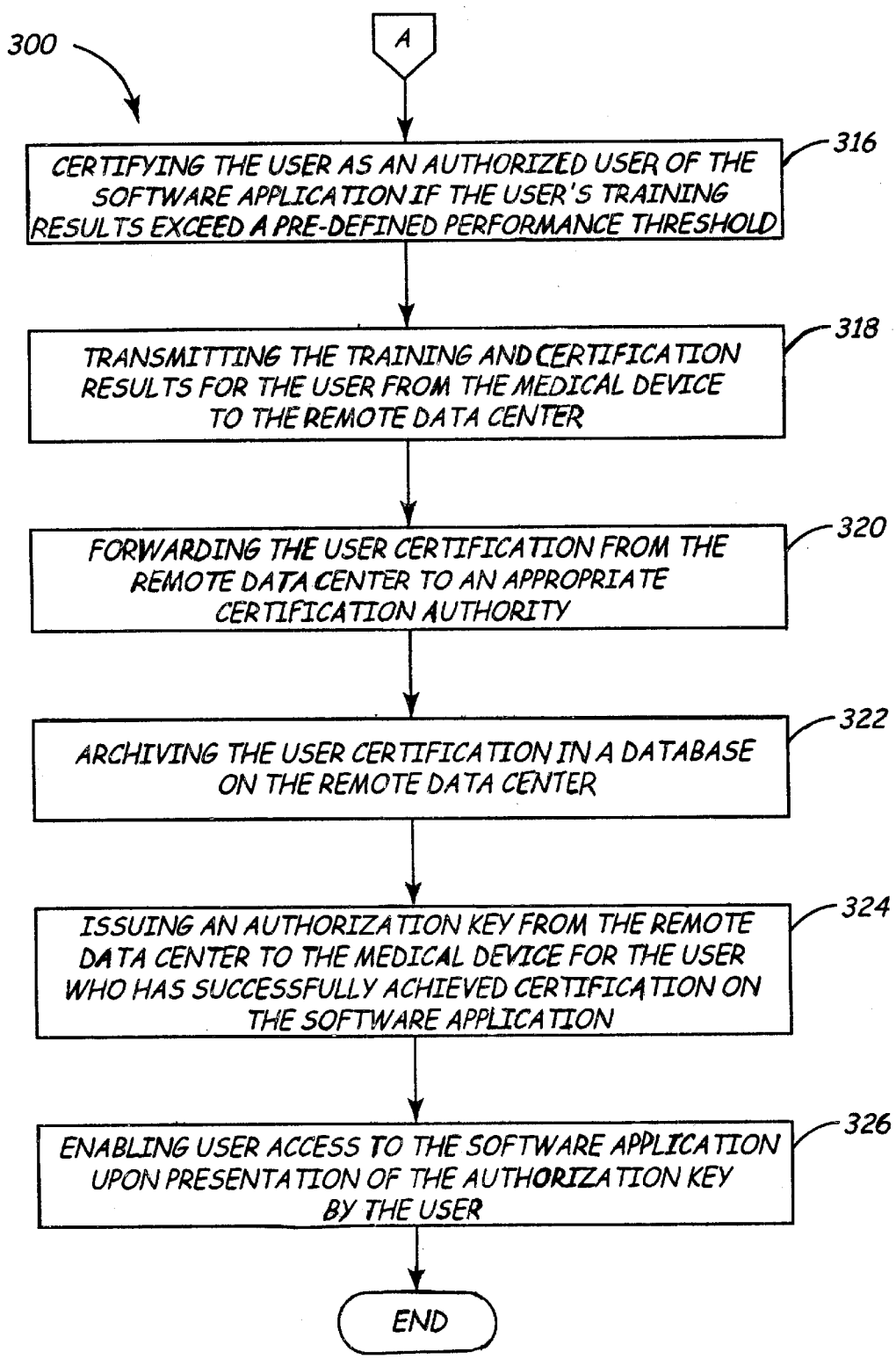

FIGS. 8A and 8B illustrate a flow chart of a method for remote delivery of software-based training for a medical device, such as programmer 20. The method begins by connecting the operator of the medical device to computer 222 via information network link 226, as indicated at step 302. The operator first connects to a self-study training component via information network link 226, and upon connection, authenticator 264 authenticates the operator as an authorized training and certification candidate for the advanced software application 242 on programmer 20, as indicated at step 304.

A training module is then selected by the operator on computer 222 corresponding to one of the software applications for monitoring patient data 242 for which the operator requests certification, as indicated at step 306. Next, as indicated at step 308, the training module is transferred from computer 222 to programmer 20 via information network link 226.

At step 310, a set of one or more skill-based activities 240 corresponding to the training module selected on computer 222 is executed by the operator on programmer 20. After the operator has completed executing the set of one or more skill-based activities 240 on programmer 20, a set of training results is generated for the operator as indicated at step 312. Next, at step 314, the operator's training results are analyzed. If the operator's training results exceed a pre-defined performance level, the operator is certified as an authorized operator for the specific software application, as indicated at step 316. The operator's training results are then transmitted from programmer 20 to computer 222, as indicated at step 318. At step 320, if the operator has achieved certification, the operator certification results are forwarded from computer 222 to the appropriate certification authority 246. Operator certification is also archived in server database 229 on computer 222, as indicated at step 322. Next, an authorization key is issued and transmitted back to programmer 20 for the certified operators, as indicated at step 324. Finally, the operator accesses the software application for monitoring patient data 242 upon which the operator has received certification by utilizing the authorization key, as indicated at step 326.

Accordingly, the present invention provides inter alia, a remote training, certification, authorization and authentication for operators to manage programmers worldwide. Generally, in the context of the invention, all programmers located proximate to IMDs or patients with IMDs and distributed globally are connected to an expert data center to share software upgrades and access archived data. The programmer functions as an interface between the remotely located expert data center and the IMDs. Further, procedural functions such as monitoring the performance of the IMDs, upgrading software in the IMDs, upkeep and maintenance of the IMDS and related functions are implemented via the programmer. The preferably telemetric and yet local interaction between the programmer and the IMDs needs to be managed by a qualified operator. In order to facilitate the just-in-time patient care at the location of the patient, the invention provides a highly efficient training system for the operator. The operator, via the programmer, is preferably wirelessly linked to a remote expert data center. This scheme enables the dissemination of software and training of the operators worldwide while maintaining a high standard of patient care at reduced costs.

Although specific embodiments of the invention have been set forth herein in some detail, it is understood that this has been done for the purposes of illustration only and is not to be taken as a limitation on the scope of the invention as defined in the appended claims. It is to be understood that various alterations, substitutions, and modifications may be made to the embodiment described herein without departing from the spirit and scope of the appended claims.

What is claimed is:

1. An interactive medical device operations training system comprising:
 a remote expert data center, said expert data center including training management software and databases for remotely administering skill-based training of an operator for an implanted medical device programmer;
 a programmer for use at a patient location and adapted to be in data communication with a medical device implanted in a patient, said programmer serving to manage the operation of the implanted medical device including acquisition of patient data through a plurality of software applications resident on the programmer and having training software operable with a skill-based simulation module for supervising training of an operator in the use of the resident software applications; and a bi-directional communications link establishing operable data communications between the programmer and the remote expert data center including a request for training issued by the programmer and the servicing of the request by the expert data center.

2. The system of claim 1, wherein the skill-based simulation module resides in the remote expert data center and is downloaded therefrom to the programmer over the bi-directional communications link in servicing a training request.

3. The system of claim 1, wherein the IMD is in data communications with to the programmer such that the programmer acquires the patient data from the IMD.

4. The system of claim 1, wherein the bi-directional link is a telephone line.

5. The system of claim 1, wherein the bi-directional communications link is an intranet.

6. The system of claim 1, wherein the bi-directional communications link is an internet.

7. The system of claim 1, wherein bi-directional communications link is a satellite.

8. The system of claim 1, wherein the bi-directional communications link is a global positioning system.

9. The system of claim 1, wherein the bi-directional communications link includes at least two communication links selected from the group of communication links consisting of a telephone line, an intranet, an internet link, a satellite, a laser waveform, and a global positioning system.

10. The system of claim 1, wherein the skill-based simulation module resides in the programmer.

11. The system of claim 1, wherein the remote expert data center further comprises:

a database of authorized operator accounts and certification information;

an authenticator module for authenticating an operator training request;

a training module processor for processing the authenticated operator training request and generating an interactive training module corresponding to at least one skill-based simulation module, the interactive training module including a list of the software applications residing on the programmer; and a certification processor for processing, distributing, and archiving operator certification information generated by the programmer.

12. The system of claim 11, wherein the remote data center further comprises:

an application enabler for enabling operator access to the software application, residing within the interactive training module processor of the remote data center, when the operator has achieved certification on the software application.

13. The system of claim 11, wherein the programmer further comprises:

a training request generator for generating an operator training request, and for transmitting the operator training request to the remote data center;

a trainer module for receiving and executing the training module generated by the remote data center;

a certificate generator for evaluating a performance of an operator on the training module and generating operator certification data if the performance of the operator on the training module exceeds a pre-defined performance criteria; and a certificate distributor for distributing the operator certification data to a certification authority.

14. The system of claim 13, wherein the certification authority is the remote data center.

15. The system of claim 13, wherein the location of the certification authority is independent and separately located from the remote data center.

16. The system of claim 13, wherein the location of the certification authority is an electronic mail address.

17. A method for remote delivery of an interactive training software package for operations of a programmer used in conjunction with IMDs, wherein a remote data center for managing the interactive training software package is linked to the programmer via a data communication network link, and wherein at least one skill-based simulated training software program for training a technician in at least one programmer software application is accessible to the programmer, the method comprising:

connecting the programmer to the remote data center via the data communications network link;

authenticating the technician of the programmer as an authorized training candidate for the simulated training software program;

selecting a training module on the remote data center corresponding to the software program upon which the technician desires training;

transferring the training module from the remote data center to the programmer via the data communications network;

executing the set of at least one skill-based simulated training software corresponding to the training module selected on the remote data center;

generating a set of training results for the technician upon completion of the training module;

analyzing the training results for the technician;

certifying the technician as an authorized operator of the software application if the technician's training test scores exceed a pre-defined performance threshold;

transmitting the training results from the programmer to the remote data center;

forwarding the technician's certification to an appropriate certification authority;

archiving the technician's certification in a database on the remote data center; and issuing an authorization key from the remote data center to the programmer to allow the technician to perform procedures on the programmer for the software application.

18. The method of claim 17, wherein the at least one skill-based simulated training software program is located on the programmer.

19. The method of claim 17, wherein the at least one skill-based simulated training software program is located on the remote data center.

20. The method of claim 17, wherein the at least one skill-based simulated training software program is located on the programmer and the remote data center.

21. The method of claim 17, wherein the programmer's in operable data communications with a certification authority.

22. The method of claim 17, wherein the data communications network is a telephone line.

23. The method of claim 17, wherein the data communications network is an intranet.

24. The method of claim 17, wherein the data communications network is an internet.

25. The method of claim 17, wherein the data communications network is a satellite.

26. The method of claim 17, wherein the data communications network is a global positioning system.

27. The method of claim 17, wherein the data communications network includes at least two communication links selected from the group of communication links consisting of a telephone line, an intranet, an internet, a satellite, a laser wave form, and a global positioning system.

28. The method of claim 17, wherein the step of forwarding the operator certification to an appropriate certification authority is performed by the programmer.

29. The method of claim 17, wherein the step of forwarding the operator certification to an appropriate certification authority is performed by the remote data center.

30. The method of claim 17, and further comprising:
enabling operator access to the software application upon presentation of the authorization key by the operator.

31. The method of claim 17, and further comprising:
disabling operator access to the medical device software application if the operator has not successfully achieved certification on a corresponding training module.

32. A bi-directional communications link integrated with a remote web-based expert data center, wherein a programmer for an IMD is uplinked to the web-based expert data center via the bi-directional communications system, wherein remote delivery of an interactive simulated software-based training for managing the programmer is effected by importing the software-based training from the expert data center to the programmer via the bi-directional communications link, and wherein at least one skill-based training software program for training a technician to acquire proficiency in at least one software application residing on the programmer, is accessible via the programmers, the system comprising:
means for connecting the programmer to the expert data center via the bi-directional communications link;
means for authenticating the technician of the programmer as an authorized training candidate for the software application;
means for selecting a training module on the remote data center corresponding to the software application upon which the technician desires training;
means for transferring the training module from the remote data center to the programmer via the bi-directional communications link;
means for executing the at least one skill-based activity on the programmer corresponding to the training module selected on the expert data center;
means for generating a set of training results for the technician upon completion of the training module;
means for analyzing the training results for the technician;
means for certifying the technician as an authorized technician of the programmer software application if the technician's training results exceed a pre-defined performance threshold;
means for transmitting the training results for the technician from the programmer to the remote data center;
means for forwarding the technician's certification to an appropriate certification authority;
means for archiving the technician certification in a database on the computer; and
means for issuing an authorization key from the remote data center to the programmer for the technician who has successfully achieved certification for the software application.

33. The system of claim 32, wherein the programmer operates a multiplicity of implantable devices.

34. The system of claim 32, wherein the system further comprises:
means for enabling technician access to the software application on the programmer upon presentation of the authorization key by the operator.

35. The system of claim 32, and further comprising:
means for disabling the technician's access to the programmer software application if the technician has not successfully achieved certification on a corresponding training module.

36. A computer implemented interactive training software system for remote delivery of software-based certification for operating/managing a programmer used in conjunction with an implantable medical device, the system comprising:
a remote data center for managing the software-based training;
a bi-directional communications link;
a programmer coupled to the remote data center via the information bi-directional communications link network link, wherein the programmer directs and monitors the acquisition of patient data through a plurality of software applications; and
at least one skill-based certification software program for certifying a technician of the programmer in the operation of the plurality of software applications.

37. The system of claim 36, wherein the at least one skill-based certification program resides on the remote data center.

38. The system of claim 36, wherein the IMD is in data communications with the programmer such that the programmer acquires the patient data from the IMD.

39. The system of claim 36, wherein the bi-directional communications link is a telephone line.

40. The system of claim 36, wherein the bi-directional communications link is an intranet.

41. The system of claim 36, wherein the bi-directional communications link is an internet.

42. The system of claim 36, wherein the bi-directional communications link is a satellite.

43. The system of claim 36, wherein the bi-directional communications link is a global positioning system.

44. The system of claim 36, wherein the information network link includes at least one communication link selected from the group of communication links consisting of a telephone line, an intranet, an internet, a satellite, a laser waveform, and a global positioning system.

45. The system of claim 36, wherein the set of at least one skill-based certification program resides on the programmer.

46. The system of claim 45, wherein the remote data center further comprises:
a database of authorized operator accounts and certification information;
an authenticator module for authenticating an operator training request;
a certification processor for processing the authenticated operator training request and generating a certification module corresponding to at least one software applications, the certification module including a selected list of the at least one skill-based activities residing on the programmer; and a certification distributor for distributing and archiving operator certification information generated by the programmer.

47. The system of claim 46, wherein the remote data center further comprises:

an application enabler for enabling the technician to access the software application residing within a certification processor in the remote data center when the technician has achieved certification on the software application.

48. The system of claim 36, wherein the programmer further comprises:

a training request generator for generating a technician training request, and for transmitting the request to the remote data center;

a trainer module for receiving and executing the training module generated by the remote data center;

a certificate generator for evaluating a performance of the technician on the training module and generating technician certification data if the performance of the technician on the training module or exceeds a pre-defined performance criteria; and a certificate distributor for transmitting the technician's certification data to a certification authority.

49. The system of claim 48, wherein the certification authority is the remote data center.

50. The system of claim 48, wherein the location of the certification authority is independent of the remote data center and globally located elsewhere.

51. The system of claim 48, wherein the location of the certification authority is an electronic mail address.

52. A method for remote delivery of an interactive software-based certification document to certify trained manager's in the operations of a programmer used in conjunction with IMDs wherein a remote data center for managing the software-based certification is linked to the programmer via a bi-directional communications link, and wherein at least one skill-based certification software program for certifying a technician for a specific software application for controlling and monitoring the programmer is downloaded to the programmer, the method comprising:

connecting the programmer to the remote medical device via the bi-directional communications link;

authenticating the technician of the programmer as an authorized certification candidate for the software application;

selecting a certification module on the remote data center corresponding to the software application upon which the technician desires certification;

transferring the certification module from the remote data center to the programmer via the bi-directional communications link;

executing the set of at least one skill-based activities corresponding to the certification module selected on the remote data center;

generating a set of training results for the technician upon completion of the certification module;

analyzing the certification results for the technician;

certifying the operator as an authorized technician of the software application if the technician's certification results exceed a pre-defined performance threshold;

transmitting the certification results for the technician from the programmer to the remote data center;

forwarding the technician certification to an appropriate certification authority;

archiving the technician certification in a database on the remote data center; and issuing an authorization key from the remote data center to the programmer for the technician.

53. The method of claim 52, wherein the at least one skill-based certification software-based program is located on the programmer.

54. The method of claim 52, wherein the set of at least one skill-based certification software-based program is located on the remote data center.

55. The method of claim 52, wherein the set of at least one skill-based certification software-based program is located on the programmer and the remote data center.

56. The method of claim 52, wherein the programmer is in direct data communications with the certification authority.

57. The method of claim 52, wherein the information network link is a telephone line.

58. The method of claim 52, wherein the information network link is an intranet.

59. The method of claim 52, wherein the information network link is an internet.

60. The method of claim 52, wherein the information network link is a satellite.

61. The method of claim 52, wherein the information network link is a global positioning system.

62. The system of claim 52, wherein the bi-directional communications link includes at least two communication links selected from the group of communication links consisting of a telephone line, an intranet, an internet, a satellite, a laser waveform, and a global positioning system link.

63. The method of claim 52, wherein the step of forwarding the technician's certification to an appropriate certification authority is performed by the programmer.

64. The method of claim 52, wherein the step of forwarding the technician's certification to an appropriate certification authority is performed by the remote data center.

65. The method of claim 52, and further comprising:

enabling the technician's access to the software application upon presentation of the authorization key by the operator.

66. The method of claim 52, and further comprising:

disabling access to the programmer software application if the technician has not successfully achieved certification on a corresponding training module.

67. A system for remote delivery of a software-based certification for operating/managing a programmer, wherein a remote data center monitors the software-based certification and is in operable data communications with the programmer via a bi-directional communications link, and wherein at least one skill-based interactive software program is implemented for certifying an operator after training and testing on at least one software application residing on the programmer, the system comprising;

means for authenticating the operator of the programmer as an authorized certification candidate for the software application;

means for selecting a certification module on the remote data center corresponding to the software application upon which the operator desires certification;

means for transferring the training module from the remote data center to the programmer via the bi-directional communications link;

means for executing the at least one skill-based activity on the programmer corresponding to the certification module selected on the remote data center;

means for generating a set of certification results for the operator upon completion of the certification module;

means for analyzing the certification results for the operator;

means for certifying the operator as an authorized operator of the software application if the operator's test results exceed a pre-defined performance threshold;

means for transmitting the certification results for the operator from the medical device to the remote data center;

means for forwarding the operator certification to an appropriate certification authority;

means for archiving the operator certification in a database on the remote data center; and means for issuing an authorization key from the remote data center to the programmer to permit the operator, who has successfully achieved certification, access to the software application.

68. The system of claim 67, wherein the programmer is in direct data communications with the certification authority.

69. The system of claim 67, wherein the system further comprises:

means for enabling operator access to the software application on the programmer upon presentation of the authorization key by the operator.

70. The system of claim 67 further comprising:

disabling the operator's access to the programmer software application if the operator has not successfully achieved certification on a corresponding training module.

* * * * *